United States Patent
Bhavaraju et al.

(10) Patent No.: US 9,075,910 B2
(45) Date of Patent: Jul. 7, 2015

(54) PHYSIOLOGICAL MONITOR SYSTEM FOR DETERMINING MEDICATION DELIVERY AND OUTCOME

(75) Inventors: Naresh Chandra Bhavaraju, San Diego, CA (US); Carl Frederick Edman, San Diego, CA (US); Michael Wayne MacCollum, Poway, CA (US); Darrel Dean Drinan, San Diego, CA (US)

(73) Assignee: PhiloMetron, Inc., San Diego, CA (US)

( * ) Notice: Subject to any disclaimer, the term of this patent is extended or adjusted under 35 U.S.C. 154(b) by 1021 days.

(21) Appl. No.: 13/046,280

(22) Filed: Mar. 11, 2011

(65) Prior Publication Data

US 2011/0224912 A1 Sep. 15, 2011

Related U.S. Application Data

(60) Provisional application No. 61/340,049, filed on Mar. 11, 2010.

(51) Int. Cl.
*G06F 19/00* (2011.01)
*A61B 5/00* (2006.01)

(52) U.S. Cl.
CPC .............. *G06F 19/3456* (2013.01); *A61B 5/00* (2013.01)

(58) Field of Classification Search
CPC .................................................. G06F 19/3456
USPC ........................................................... 702/19
See application file for complete search history.

(56) References Cited

U.S. PATENT DOCUMENTS

| | | | |
|---|---|---|---|
| 4,402,694 | A | 9/1983 | Ash et al. |
| 4,805,621 | A | 2/1989 | Heinze et al. |
| 4,854,328 | A | 8/1989 | Pollack |
| 4,860,753 | A | 8/1989 | Amerena |
| 4,870,753 | A | 10/1989 | Pfeffer et al. |
| 4,966,158 | A | 10/1990 | Honma et al. |
| 5,001,436 | A | 3/1991 | Scot et al. |
| 5,038,109 | A | 8/1991 | Goble et al. |
| 5,086,781 | A | 2/1992 | Bookspan |
| 5,242,415 | A | 9/1993 | Kantrowitz et al. |
| 5,297,556 | A | 3/1994 | Shankar |
| 5,335,667 | A | 8/1994 | Cha et al. |
| 5,353,802 | A | 10/1994 | Ollmar |
| 5,375,604 | A | 12/1994 | Kelly et al. |
| 5,445,008 | A | 8/1995 | Wachter et al. |
| 5,511,553 | A | 4/1996 | Segalowitz |

(Continued)

FOREIGN PATENT DOCUMENTS

| | | |
|---|---|---|
| EP | 1072994 A2 | 1/2001 |
| EP | 1629772 A1 | 3/2006 |

(Continued)

OTHER PUBLICATIONS

Samarati et al. Data Security. Wiley Encyclopedia of Electrical and Electronics Engineering. Dec. 27, 1999.

(Continued)

*Primary Examiner* — Bryan Bui

(57) ABSTRACT

A method is described for the determination of the taking of a medication utilizing at least one physiological parameter monitoring platform. In addition, the method also may enable the determination of physiological effects or events resultant from the taking of a medication (or lack thereof) through the use of one or more physiological monitoring platforms.

20 Claims, 6 Drawing Sheets

(56) References Cited

U.S. PATENT DOCUMENTS

| | | |
|---|---|---|
| 5,558,638 A | 9/1996 | Evers et al. |
| 5,634,468 A | 6/1997 | Platt et al. |
| 5,720,770 A | 2/1998 | Nappholz et al. |
| 5,732,710 A | 3/1998 | Rabinovich et al. |
| 5,738,107 A | 4/1998 | Martinsen et al. |
| 5,749,369 A | 5/1998 | Rabinovich et al. |
| 5,752,976 A | 5/1998 | Duffin et al. |
| 5,779,630 A | 7/1998 | Fein et al. |
| 5,788,643 A | 8/1998 | Feldman |
| 5,833,603 A | 11/1998 | Kovacs et al. |
| 5,879,292 A | 3/1999 | Sternberg et al. |
| 5,931,764 A | 8/1999 | Freeman et al. |
| 5,935,066 A | 8/1999 | Harris |
| 5,941,829 A | 8/1999 | Saltzstein et al. |
| 5,944,659 A | 8/1999 | Flach et al. |
| 5,964,703 A | 10/1999 | Goodman et al. |
| 5,964,720 A | 10/1999 | Pelz |
| 5,980,429 A | 11/1999 | Nashner |
| 5,987,352 A | 11/1999 | Klein et al. |
| 6,010,465 A | 1/2000 | Nashner |
| 6,016,686 A | 1/2000 | Thundat |
| 6,047,203 A | 4/2000 | Sackner et al. |
| 6,074,345 A | 6/2000 | van Oostrom et al. |
| 6,083,248 A | 7/2000 | Thompson |
| 6,092,530 A | 7/2000 | Weissman et al. |
| 6,093,146 A | 7/2000 | Filangeri |
| 6,095,987 A | 8/2000 | Shmulewitz et al. |
| 6,125,297 A | 9/2000 | Siconolfi |
| 6,175,752 B1 | 1/2001 | Say et al. |
| 6,198,394 B1 | 3/2001 | Jacobsen et al. |
| 6,213,942 B1 | 4/2001 | Flach et al. |
| 6,225,901 B1 | 5/2001 | Kail, IV |
| 6,244,873 B1 | 6/2001 | Hill et al. |
| 6,265,978 B1 | 7/2001 | Atlas |
| 6,287,252 B1 | 9/2001 | Lugo |
| 6,289,238 B1 | 9/2001 | Besson et al. |
| 6,315,719 B1 | 11/2001 | Rode et al. |
| 6,331,160 B1 | 12/2001 | Bardy |
| 6,339,722 B1 | 1/2002 | Heethaar et al. |
| 6,358,201 B1 | 3/2002 | Childre et al. |
| 6,360,888 B1 | 3/2002 | McIvor et al. |
| 6,370,426 B1 | 4/2002 | Campbell et al. |
| 6,411,853 B1 | 6/2002 | Millot et al. |
| 6,413,255 B1 | 7/2002 | Stern |
| 6,416,471 B1 | 7/2002 | Kumar et al. |
| 6,441,747 B1 | 8/2002 | Khair et al. |
| 6,459,917 B1 | 10/2002 | Gowda et al. |
| 6,459,930 B1 | 10/2002 | Takehara et al. |
| 6,482,158 B2 | 11/2002 | Mault |
| 6,496,705 B1 | 12/2002 | Ng et al. |
| 6,506,152 B1 | 1/2003 | Lackey et al. |
| 6,512,949 B1 | 1/2003 | Combs et al. |
| 6,524,239 B1 | 2/2003 | Reed et al. |
| 6,540,672 B1 | 4/2003 | Simonsen et al. |
| 6,544,174 B2 | 4/2003 | West et al. |
| 6,551,252 B2 | 4/2003 | Sackner et al. |
| 6,554,798 B1 | 4/2003 | Mann et al. |
| 6,577,893 B1 | 6/2003 | Besson et al. |
| 6,591,122 B2 | 7/2003 | Schmitt |
| 6,595,929 B2 | 7/2003 | Stivoric et al. |
| 6,605,038 B1 | 8/2003 | Teller et al. |
| 6,615,077 B1 | 9/2003 | Zhu et al. |
| 6,631,292 B1 | 10/2003 | Liedtke |
| 6,632,158 B1 | 10/2003 | Nashner |
| 6,636,754 B1 | 10/2003 | Baura et al. |
| 6,643,543 B2 | 11/2003 | Takehara et al. |
| 6,645,142 B2 | 11/2003 | Braig et al. |
| 6,699,188 B2 | 3/2004 | Wessel |
| 6,714,813 B2 | 3/2004 | Ishigooka et al. |
| 6,790,178 B1 | 9/2004 | Mault et al. |
| 6,823,212 B2 | 11/2004 | Pinyayev |
| 6,897,788 B2 | 5/2005 | Khair et al. |
| 6,963,035 B2 | 11/2005 | Honda et al. |
| 6,963,772 B2 | 11/2005 | Bloom et al. |
| 6,980,852 B2 | 12/2005 | Jersey-Willuhn et al. |
| 7,079,899 B2 | 7/2006 | Petrofsky |
| 7,184,820 B2 | 2/2007 | Jersey-Willuhn et al. |
| 7,191,000 B2 | 3/2007 | Zhu et al. |
| 7,261,690 B2 | 8/2007 | Teller et al. |
| 7,285,090 B2 | 10/2007 | Stivoric et al. |
| 7,499,745 B2 | 3/2009 | Littrup et al. |
| 7,889,069 B2 | 2/2011 | Fifolt et al. |
| 8,430,817 B1* | 4/2013 | Al-Ali et al. .................. 600/301 |
| 2001/0051774 A1 | 12/2001 | Littrup et al. |
| 2002/0019584 A1 | 2/2002 | Schulze et al. |
| 2002/0019586 A1 | 2/2002 | Teller et al. |
| 2002/0045836 A1 | 4/2002 | Alkawwas |
| 2002/0133378 A1 | 9/2002 | Mault et al. |
| 2002/0156351 A1 | 10/2002 | Sagel |
| 2002/0169387 A1 | 11/2002 | Marmaropoulos et al. |
| 2003/0004403 A1 | 1/2003 | Drinan et al. |
| 2003/0120170 A1 | 6/2003 | Zhu et al. |
| 2003/0149344 A1 | 8/2003 | Nizan |
| 2003/0199783 A1 | 10/2003 | Bloom et al. |
| 2003/0223905 A1 | 12/2003 | Moerman |
| 2004/0019292 A1 | 1/2004 | Drinan et al. |
| 2004/0030258 A1 | 2/2004 | Williams et al. |
| 2004/0039254 A1 | 2/2004 | Stivoric et al. |
| 2004/0077934 A1 | 4/2004 | Massad |
| 2004/0127895 A1 | 7/2004 | Flock et al. |
| 2004/0133081 A1 | 7/2004 | Teller et al. |
| 2004/0147977 A1 | 7/2004 | Petrofsky |
| 2004/0152957 A1 | 8/2004 | Stivoric et al. |
| 2004/0171962 A1 | 9/2004 | Leveque et al. |
| 2004/0254624 A1 | 12/2004 | Johnson |
| 2005/0021372 A1 | 1/2005 | Mikkelsen et al. |
| 2005/0070778 A1 | 3/2005 | Lackey et al. |
| 2005/0101875 A1 | 5/2005 | Semler et al. |
| 2005/0113650 A1 | 5/2005 | Pacione et al. |
| 2006/0058593 A1 | 3/2006 | Drinan et al. |
| 2006/0089592 A1 | 4/2006 | Kadhiresan et al. |
| 2006/0264775 A1 | 11/2006 | Mills et al. |
| 2006/0270942 A1 | 11/2006 | McAdams |
| 2007/0048691 A1 | 3/2007 | Brown |
| 2007/0100666 A1 | 5/2007 | Stivoric et al. |
| 2007/0219419 A1 | 9/2007 | KenKnight et al. |
| 2008/0033502 A1 | 2/2008 | Harris et al. |
| 2008/0146334 A1 | 6/2008 | Kil |
| 2008/0311968 A1 | 12/2008 | Hunter |
| 2008/0319796 A1 | 12/2008 | Stivoric et al. |
| 2009/0048070 A1 | 2/2009 | Vincent et al. |
| 2010/0016692 A1* | 1/2010 | Addison et al. ............... 600/324 |
| 2010/0049004 A1* | 2/2010 | Edman et al. .................. 600/300 |

FOREIGN PATENT DOCUMENTS

| | | |
|---|---|---|
| JP | 1998-295652 | 11/1998 |
| JP | 2000-023935 | 1/2000 |
| JP | 2001-353130 | 12/2001 |
| JP | 2007-505412 A | 3/2007 |
| WO | WO 9840009 A1 | 9/1998 |
| WO | WO 0054237 A1 | 9/2000 |
| WO | WO 0137726 A1 | 5/2001 |
| WO | WO 03015005 A2 | 2/2003 |
| WO | WO 2004049937 A1 | 6/2004 |
| WO | WO 2005029242 A2 | 3/2005 |
| WO | WO 2009079366 A2 | 6/2009 |

OTHER PUBLICATIONS

Jaskowski. Evaluation of the healing process of skin wounds by means of skin absolute value of electrical impedance. Dermatol. Mon.schr. 172 (1986) 223-228.
U.S. Appl. No. 10/032,765, Mar. 6, 2003 non-final office action.
PCT application US2002/020006, May 29, 2003 ISR.
U.S. Appl. No. 10/032,765, Dec. 4, 2003 non-final office action.
U.S. Appl. No. 10/032,765, May 18, 2004 non-final office action.
PCT application US2002/020006, Aug. 5, 2004 IPER.
PCT application US2004/027106, Feb. 18, 2005 ISR.
U.S. Appl. No. 10/032,765, Aug. 25, 2005 final office action.
U.S. Appl. No. 11/219,348, Jan. 24, 2006 ISR.
PCT application US2004/027106, Feb. 21, 2006 IPRP.
U.S. Appl. No. 10/922,370, Jun. 6, 2006 non-final office action.

(56) References Cited

OTHER PUBLICATIONS

AU patent application 2004266725, Nov. 17, 2006 office action.
U.S. Appl. No. 10/922,370, Dec. 29, 2006 final office action.
PCT application US2005/031442, Mar. 6, 2007 IPRP.
PCT application US2005/031441, Mar. 6, 2007 IPRP.
U.S. Appl. No. 10/922,370, Jun. 18, 2007 non-final office action.
U.S. Appl. No. 11/219,327, Aug. 14, 2007 non-final office action.
U.S. Appl. No. 11/219,348, Jan. 3, 2008 non-final office action.
JP patent application, Feb. 8, 2008 office action.
U.S. Appl. No. 10/922,370, May 14, 2008 final office action.
U.S. Appl. No. 11/219,327, May 16, 2008 final office action.
U.S. Appl. No. 11/219,348, Oct. 21, 2008 final office action.
U.S. Appl. No. 11/841,947, Jan. 29, 2009 non-final office action.
EP patent application 02802911, Feb. 3, 2009 supplemental search report.
EP patent application 04786547, Feb. 23, 2009 supplemental search report.
EP patent application 02802911, Jun. 10, 2009 office action.
U.S. Appl. No. 11/219,327, Jun. 24, 2009 non-final office action.
EP patent application 04786547, Jul. 13, 2009 office action.
U.S. Appl. No. 10/922,370, Aug. 3, 2009 non-final office action.
AU patent application 2004266725, Aug. 10, 2009 office action.
U.S. Appl. No. 11/402,225, Sep. 29, 2009 non-final office action.
U.S. Appl. No. 11/841,947, Nov. 20, 2011 final office action.
U.S. Appl. No. 11/410,519, Nov. 30, 2009 non-final office action.
PCT application US2009/002473, Dec. 23, 2009 ISR.
U.S. Appl. No. 11/219,348, Jan. 12, 2010 non-final office action.
U.S. Appl. No. 11/219,327, Apr. 1, 2010 final office action.
EP patent application 04786547, Jun. 29, 2010 office action.
U.S. Appl. No. 11/410,519, Sep. 2, 2010 final office action.
U.S. Appl. No. 11/402,225, Sep. 15, 2010 final office action.
EP patent application 02802911, Sep. 29, 2010 office action.
PCT application US2009/002473, Oct. 26, 2010 IPRP.
CA patent application 2451526, Feb. 2, 2011 office action.
U.S. Appl. No. 11/402,225, Apr. 13, 2011 non-final office action.
U.S. Appl. No. 11/410,519, Apr. 13, 2011 non-final office action.
PCT application US2010/002508, Apr. 22, 2011 ISR.
U.S. Appl. No. 12/386,614, Apr. 29, 2011 non-final office action.
EP patent application 04786547, Aug. 25, 2011 office action.
JP patent application 2006-524077, Sep. 6, 2011 office action.
EP patent application 11174980, Sep. 29, 2011 search report.
PCT application US2011/028160, Sep. 29, 2011 ISR.
U.S. Appl. No. 11/219,327, Oct. 11, 2011 non-final office action.
U.S. Appl. No. 12/828,110, Oct. 13, 2011 non-final office action.
CA patent application 2539547, Jan. 9, 2012 office action.
U.S. Appl. No. 11/410,519, Jan. 19, 2012 final office action.
U.S. Appl. No. 11/402,225, Jan. 20, 2012 final office action.
PCT application US2010/002508, Mar. 20, 2012 IPRP.
U.S. Appl. No. 12/807,835, Mar. 21, 2012 non-final office action.
PCT application US2011/028160, Sep. 11, 2012 IPRP.
U.S. Appl. No. 11/841,947, Jul. 31, 2013 non-final office action.
U.S. Appl. No. 10/032,765, Dec. 20, 2005 notice of allowance.
U.S. Appl. No. 10/922,370, Apr. 21, 2010 notice of allowance.
AU patent application 2008246222, Sep. 21, 2010 office action.
AU patent application 2011202767, Mar. 6, 2012 office action.
EP patent application 09735540.8, Sep. 9, 2013 suppl search.
U.S. Appl. No. 11/402,225, Sep. 13, 2013 notice of allowance.
U.S. Appl. No. 11/410,519, Sep. 17, 2013 notice of allowance.
AU patent application 2012203630, Mar. 8, 2014 office action.
AU patent application 2009238661, Jan. 2, 2015 office action.
EP patent application 09735540.8, Jan. 26, 2015 office action.

* cited by examiner

PHYSIOLOGICAL MONITOR SYSTEM FOR DETERMINING MEDICATION DELIVERY AND OUTCOME

FIELD OF THE INVENTION

The present invention relates to a system enabling the determination of the taking of a medication utilizing at least one physiological parameter monitoring platform. In addition, the system also may enable the determination of physiological effects or events resultant from the taking of a medication (or lack thereof) through the use of one or more physiological monitoring platforms.

BACKGROUND

Lack of compliance in the taking of recommended medications including the following of therapeutic treatment regimens may lead to serious health consequences for patients and increase the overall cost of care. For example, failure to take a prescribed medication or taking the medication at incorrect times may result in a prolongation or possible accentuation of the disease state. Conversely, over-dosage may result in adverse or non-intended side effects thereby also possibly negatively impacting the health and well being of the patient.

In many instances, the patient or caregiver may not be able to objectively ascertain whether or not a medication has been taken in the appropriate fashion or not. In order to provide an independent assessment of medication delivery and uptake, numerous solutions have been proposed.

For instance, Kell (U.S. Pat. No. 5,652,146) teaches the use of monitoring urine in order to ascertain patient compliance regarding whether or not a medication has been taken or not as well as estimating the dosage of the medication within the patient. However, this form of monitoring still requires compliance on the part of the patient for obtaining the necessary urine sample and requires similar metabolic profiles to be shared amongst individuals in order to enable estimation of drug ingestion and levels.

Alternatively, Katzman (U.S. Pat. No. 6,180,414) teaches the use of breath monitoring for drug metabolites, as compared to urine, to thereby ascertain whether a drug has been ingested or not. However, this approach likewise is dependent on the metabolic profile of the individual which may vary from expected patterns based on disease state, co-morbidities, genetics, lifestyle, etc.

To improve upon the need for metabolic detection and analysis, Melker, et al. (US Patent Application No. 2005/0054942) teaches the use of adjuvant to the drug or agent which then may be detected in the breath as a defined odor. In similar fashion, Kell (U.S. Pat. No. 5,776,783) teaches the addition of markers which may be added to drug formulations and then detected in urine to enable determination of drug ingestion.

To supersede the need for detection of a metabolite and/or absorbed/metabolized marker associated with an ingested drug, others have proposed the use of direct signaling of drug ingestion. In particular, the use of radio transmitters or radiofrequency tags (RF tag) has been proposed by numerous individuals. For example, Covannon, et al. (U.S. Pat. No. 7,616,111) teaches the use of an ingestible RF tag to monitor the consumption of medicines. Likewise, Danowski, et al., (U.S. Pat. No. 7,382,263) teaches the use of a shielded RF tag to monitor the consumption of drugs. In yet another related form, Zdeblick et al., (US Patent Application No. 20080284599) teaches the use of a transmitter which becomes activated upon digestion and exposure to body fluids such as stomach acids, etc.

However, none of the above methods for determining compliance to medicine ingestion considers whether the ingested materials result in a desired physiological outcome or not. What is needed is a system that enables not only determination of compliance to medication use but also gauges the physiological outcomes associated with compliance such that medication may be more properly prescribed (e.g. titrated) and the taking of the medication in a desired fashion verified.

SUMMARY OF THE INVENTION

The invention described herein presents a novel system for the determination of the taking of medication based upon measurement of one or more physiological parameters followed by analysis and identification of one or more physiological signatures associated with the taking of medication. In preferred embodiments of the invention, a plurality of measured physiological data are employed to compile a physiological signature related to the taking of one or more medications and/or of signatures associated with the possible occurrence and severity of side effects associated with the taking of one or more medications.

In one form of the present invention, the system enables the determination (yes/no) of the taking of the medication. To accomplish this determination, one or more measured physiological signatures associated either with the taking of the medication, e.g. swallowing, or signatures associated an outcome arising from the ingestion of the medication, e.g. relief of one or more symptoms for which the medication is taken.

In related embodiments, said physiological determination is coupled by one or more additional non-physiological measured events to enable determination of the taking of one or more medications. In such embodiments, signals associated with the removal or dispensing of medication from a package or container may be employed. Alternatively, signals associated with the handling or delivery of medication may be employed. In still other embodiments, one or more compounds not having medicinal value but associated with the medication may be employed to enable measurable signals and thereby facilitate the determination that medicine has been taken.

In other forms of the present invention, an assessment of the dosage of the taken medicine may be made, based upon one or more measured physiological parameters. Such assessment may include determination of whether one or more unwanted side effects may have occurred or may occur as well as whether one or more desired symptoms and/or underlying disease conditions has been relieved.

In other embodiments of the present invention, a baseline set of physiological parameters may be created through the measurement of one or more physiological measurements. Such baseline data may thereby be employed to facilitate subsequent determination of physiological change associated with the taking of medication, tailored to the individual.

DETAILED DESCRIPTION OF THE INVENTION

Figure 1:
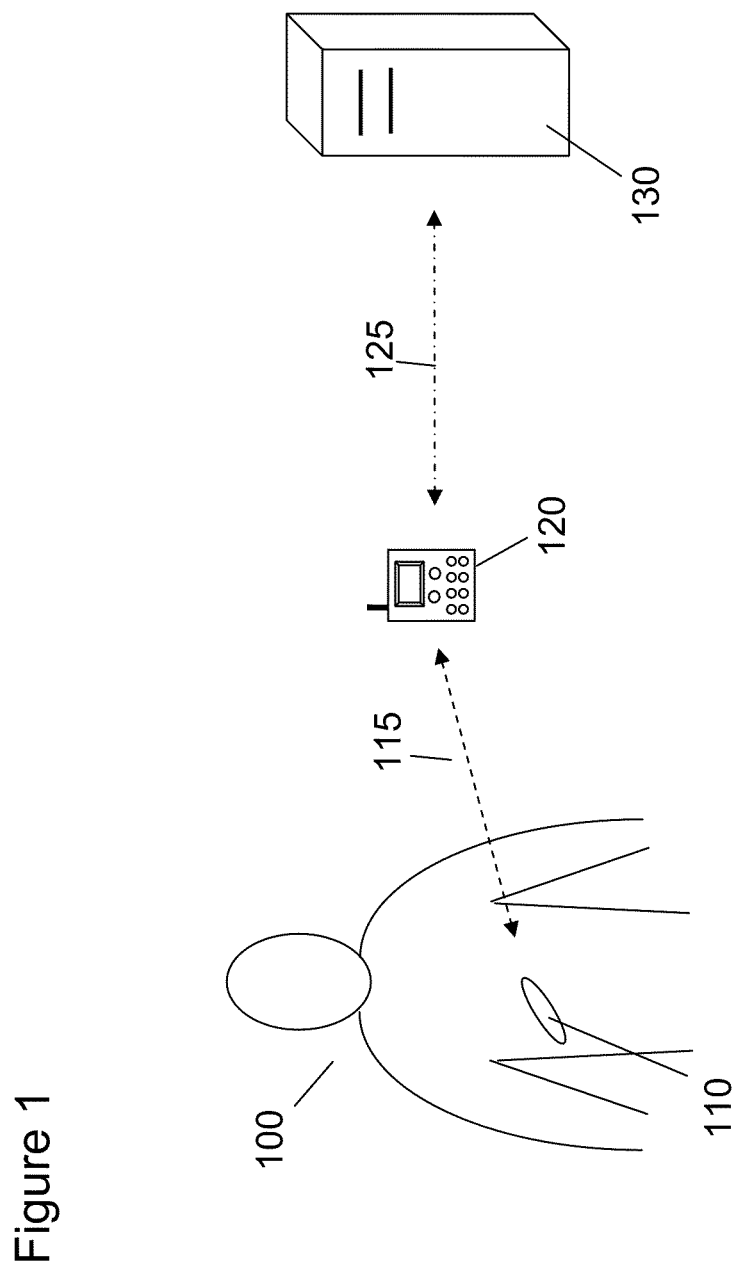
FIG. 1—Illustration of one embodiment of the system of the present invention.

The invention generally relates to a novel method and system for the assessment of the taking of one or medications by the measurement of one or more physiological parameters. A general outline of a preferred embodiment of the system of the present invention is presented in FIG. 1. As shown, patient 100 has affixed to a body region monitoring platform 110 enabling the measurement of one or more physiological parameters. Communication of measured data or transforms of the measured data may then be wirelessly conveyed, as indicated by dash arrow 115, to local data collection unit 120. Said data may be further analyzed and results displayed on data collection unit 120. Alternatively, all or some of said data and/or analysis may then be further conveyed to one or more remote data management systems, 130, as indicated by staggered dash line 125. Within remote data management system 130 further review and analysis of the data may occur as well as additional review by one or more third parties. Forms of this system having on-body monitoring platforms comprised of biointerface heads and control/communication modules, data collection units, and remote data management systems are described in U.S. Pat. No. 7,044,911 and related filings which are incorporated in their entirety by this mention herein. A more complete description of each of these components are presented below.

Monitoring Platform

Medications may exhibit different temporal responses between individuals and/or types of medications due to differing route of administration, distribution or sequestration within the body, metabolism and/or excretion. Accordingly, advantageous use may be made of forms of physiological monitoring wherein one or more physiological measurements are made, either periodically, upon demand or in effectively continuous fashion over a period of time.

In preferred embodiments of the present invention, one or more physiological monitoring platforms are affixed to one or more body regions, e.g. by means of adhesive, such that multiple measurements may be automatically obtained with minimal patient compliance. In other embodiments, monitoring platforms may be invasive or implanted within the body. In yet other embodiments, such monitoring platforms may reside off of the body, e.g. glucose tests employing test strips using blood or the testing of collected body fluid samples.

In general form, monitoring platforms may incorporate one or more sensors for the measurement of one or more physiological parameters. To enable the measurement, storage, analysis and/or transmission (or display) of such measured data, monitoring platforms may incorporate necessary electronic circuitry, clocks and power sources. Such circuitry and power sources are well known to those skilled in the art of electronics.

In preferred embodiments, a monitoring platform may employ materials and structures suitable for its intended use, e.g. if the monitoring platform utilizes electrode sensors and is affixed to the body by means of adhesives, the materials in contact with the body surface would preferably be biocompatible. In similar fashion, the housing of such monitoring platform if intended to be affixed to the body for an extended period of time may be water resistant and in general the platform may be constructed of flexible or conformable elements to improve patient comfort during use.

A variety of physiological parameters may be measured by one or more monitoring platforms. Measured parameters may include, but are not limited to the following:

Physical—motion, anthropometrics (e.g. waist, height, weight measurements), tissue structure and composition Biochemical—cellular, tissue, organ or whole body biochemical structure/functions, e.g. cellular respiration and proliferation, circulating or locally concentrated small molecules/proteins/peptides, catabolic materials (certain ketones, lactic acid), blood chemistry (e.g. ion composition, pH, carbon dioxide, oxygen, blood nitrogen), circulating nutrients (e.g. glucose, fatty acids, lipids and amino acids)

Metabolic—vital signs (heart rate, blood pressure, respiration rate, temperature), basal metabolic rate, hydration status Nervous System—central and/or peripheral parasympathetic or sympathetic activity, cognitive functions, psychological status (e.g. mood), headaches, sleep patterns Immune System—circulating immune cell types and populations, target responses to specific antigens, immune signaling molecules such as histamine, cytokines, etc.

Cardiovascular/Pulmonary—heart functionality (ECG, heart rate variability), respiratory rate/volume, arterial resistance/stiffening, arterial blockage, venous return, peripheral circulation, microcapillary proliferation/circulation Endocrine/Paracrine—hormones or endogenous agents (e.g. insulin/glucagon, leptin, steroid hormones, biogenic amines)

Organs—size, composition and functionality, (e.g. kidney functionality, liver functionality, adipose tissue disposition, skin thickness/plasticity)

Figure 2:
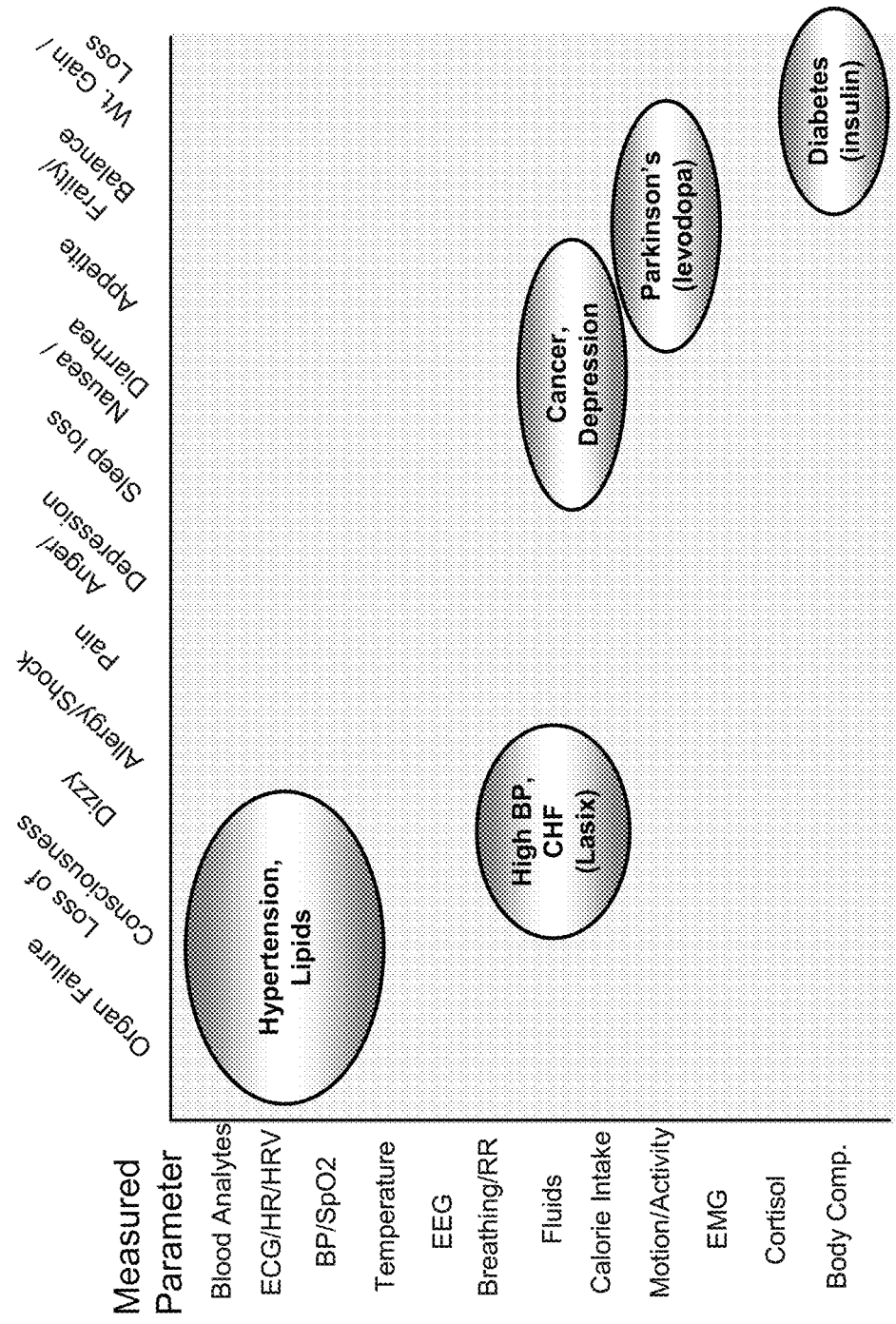
FIG. 2—Diagram illustrating the relationship between measured physiological parameters and symptoms for select disease states.

Muscular/Skeletal—electromuscular activity (e.g. latent or stimulated), strength, composition, oxygenation, density Gastro-Intestinal—digestive activity and efficiency, gut microfauna population Such measured parameters may be related to one or more symptoms associated with the taking of medication, e.g. change in the targeted physiological parameter and/or the occurrence of one or more side effects. An illustration of the relationship between physiological parameters and symptoms associated with various disease states is presented in FIG. 2. As shown, one or more measured parameters may be utilized to identify one or more symptoms associated with a change in physiological status associated with the taking (or lack thereof) of one or more medications. Also illustrated in this example is that different disease conditions may utilize different medications and different measured parameters.

To measure one or more of the above parameters, one or more sensors may be employed. Such sensors may involve the exchange of one or more energies with one or more body regions. Such energies may include, but are not limited to, mechanical energies, photonic energies, electrical energies, radioactive energies, magnetic energies, acoustic energies, electromagnetic energies, and chemical energies, For example, blood oxygen and heart rate may be measured by use of photonic energies, e.g. pulse oximetry, in order to provide necessary data. Likewise, body hydration or change in hydration may be assessed through use of one or more bioelectrical impedance measurements. Still other measurements, e.g. tissue structure, may be determined by use of electromagnetic energies such as ultra wideband radar, or acoustic energies such as ultrasound energies.

Within the scope of the present invention, sensors may be employed that do not involve the direct exchange of one or more energies with one or more body regions. Such sensors may passively receive energies from a body region, e.g. temperature sensors, accelerometers for motion, ECG/EMG/EEG sensors detecting endogenously produced electrical signals, etc.

In addition, sensors may measure one or more samples obtained from a body region, including body fluids, e.g. analysis of blood, sweat, urine, saliva, tears. Likewise one or more exhaled or transpired gases may be analyzed, e.g. breath composition for ketones, etc. Likewise, fecal materials may be analyzed, e.g. for blood, microfauna, etc. Such sensors may include the use of one or more devices or technologies associated with in vitro diagnostic (IVD) devices and/or of more complicated systems, e.g. mass spectrometers.

In still other forms of the invention, a tracer or introduced agent or material may be employed to facilitate the assessment of one or more parameters. Examples of such agents may include the use of radiolabeled tracers, e.g. deuterium labeled water, to facilitate assessment of total body water and change in total body water. Likewise, agents may be supplied that preferentially are sequestered into a body region or compartment, e.g. tumor specific markers, and thereby would facilitate analysis of these tissues or organs through use of one or more measurement technologies selected to measure one or more properties inherent in these markers. In this form of the invention, the tracer, agent or material may be controlled and/or interrogated by a monitoring platform to facilitate analysis of one or more physiological parameters.

In still other embodiments, one or more physiological status parameters may be obtained through use of subjective assessment provided by the measured subject. For example, the subject may reply to an automated voice query received by telephone wherein the reply would automatically be quantified, e.g. a yes equal to a numeric value of 1 and a no being a numeric value of zero. These data may include a number of physiological parameter assessments made by the individual, including a general assessment of health status, mood, and/or specific physiological conditions, e.g. difficulty breathing. In addition, such queries may also involve self reporting regarding the taking of one or more medications. Data from such systems may be automatically collected and transmitted to one or more comparators of the present invention.

As yet a further refinement, various embodiments may employ analysis of voice patterns, speed of response, tones of voice or other parameters independent of the spoken content of the communication. For example, detection of a change in pitch or tone of an individual's response may be associated with physical illness onset and/or depression. Parameters arising from such assessments may be included within the data provided to one or more comparators for facilitating analysis of whether or not a medication has been taken or not.

In general terms, the anticipated physiology associated with a disease or condition and the associated response to medication and possible side effects may be employed in the selection of sensors to be utilized in the monitoring platform for a particular patient. In many instances, it is anticipated that a core set of physiological parameters will be employed as a general gauge of patient health status.

Figure 3:
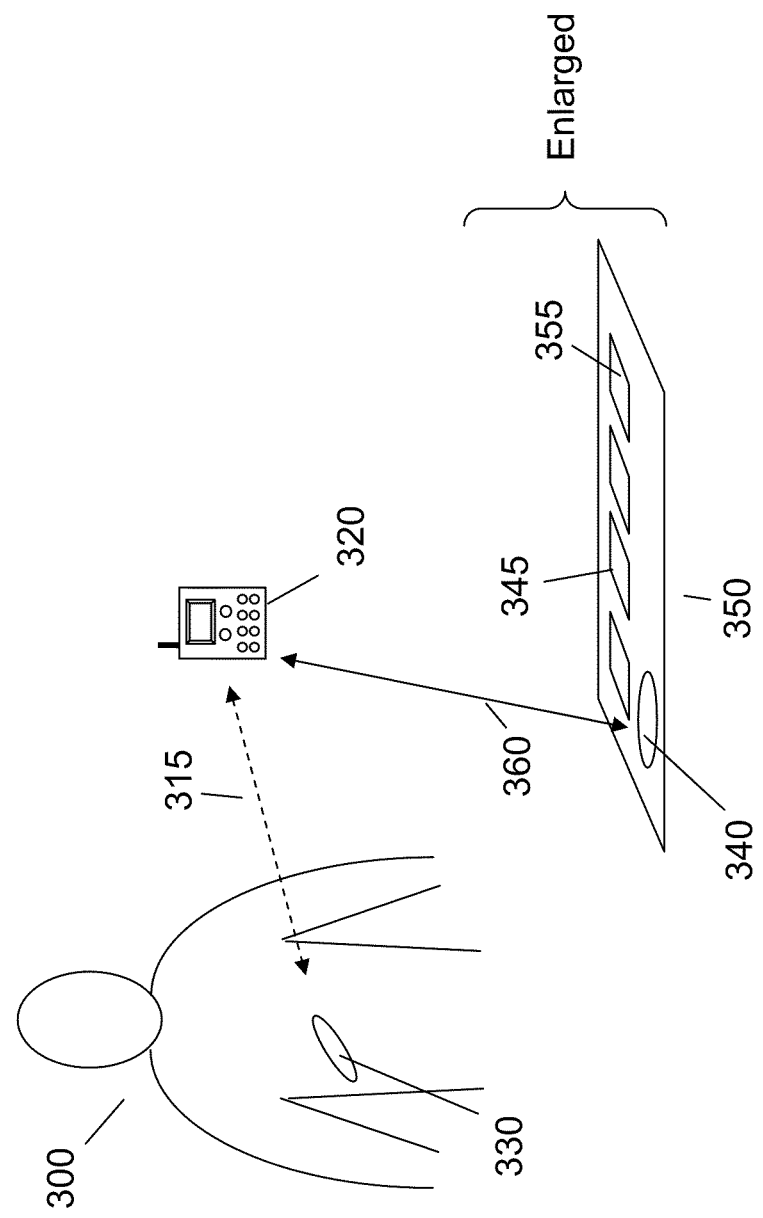
FIG. 3—Illustration of one form of the present invention employing physiological and non-physiological sensors.

In addition, use of one or more sensors not associated with the direct monitoring of a physiological parameter may be employed to facilitate analysis of the patient's taking of medication and the response to this medication. For example, as shown in FIG. 3, patient 300 has monitoring platform 330 for measuring physiological parameters and then transmitting said data (315) to data collection unit 320. Also shown is an enlarged representation of a medication container 350 wherein individual unopened 345 and opened 355 medications are contained. The action of opening an individual medication to enable taking the medication triggers a signal to be sent from circuitry unit 340 located on the medication container 350 to data collection unit 320. Such signals may be coordinated with physiological measurements to enable assessment of the taking of mediation and/or serve as time points to better enable the subsequent analysis of physiological measurements to one or more changes in physiology associated with the taking of medication.

Data Collection Unit

In a preferred embodiment, the data collection unit serves to collect the information from one or more monitoring platforms to enable the assessment of patient compliance to the taking of one or medications and the resultant response of the patient's physiology to such activity. In general terms, the data collection unit has one or more means for receiving information, including patient specific identifiers, e.g. identifiers of the monitoring platform or components therein, as well as data and information generated by one or more monitoring platforms. In preferred embodiments, measured patient data is received wirelessly however other forms of data entry, e.g. through keyboards, by voice recognition software, direct wired connection, etc. are conceivable and are included within the scope of the present invention.

In various embodiments, the data collection unit may also have one or more display functionalities, e.g. visual or audible, to enable conveyance of monitoring platform operation and/or patient status to the patient or other individual. In addition, the data display unit may store data from one or more patients to facilitate subsequent analysis and/or transfer to one or more remote monitoring systems. Such data collection units may take the form of handheld units, e.g. cell phones, or personal digital assistants, with the appropriate transmission capabilities and software to enable the present invention.

One or more comparators may be present as part of the data collection unit functionalities. Such comparators may be utilized to facilitate analysis of received data to enable the determination of medication usage as well as the associated physiological response to the medication. Comparator functionality may also reside in whole or in part in other system components, e.g. within monitoring platforms and/or remote data management systems.

A primary function of the comparator is to determine if a medication has been taken or not. In order to make this assessment, in preferred embodiments, the comparator may utilize one or more sets of data reflective of baseline status, i.e. prior to taking the medication, and compare these data to one or more sets of data to determine physiological events associated with the taken of medication.

In forms of medication which involve oral ingestion, measured physiological data may include the measurement of physical activities associated with the act of swallowing, e.g. throat muscle constrictions and/or audible signals arising from the gut. To facilitate the identification of a physiological event with medication ingestion, one or more non-physiological sensors may be employed. For example, a sensor associated with a container or packaging that wirelessly transmits a signal to a data collection unit indicating the opening of the container, when combined with the measurement within a predetermined period of time, e.g. minutes, may serve to support the likelihood that a medication has been consumed in a desired fashion.

In yet other forms of the invention, one or more signaling agents or transmitters may be associated with the medication itself such that the ingestion of the medication results in a signal that is receivable by one or more monitoring platforms.

Physiological monitoring in combination with such signals would increase the likelihood of correctly assessing that a medication has been taken in a desired fashion.

Other forms involving taking of medication, e.g. injection, may include one or more sensors placed on the medication delivery device or system that would signal that the medication is present and/or the delivery device has been activated in a desired fashion.

In still other forms of the invention where the medication does not take the form of a drug or agent but is rather a therapy or activity, e.g. physical therapy as part of rehabilitation, exercise, or smoking cessation, monitoring platform measurements may include the measurement of one or more physiological parameters associated the therapy. For example, in a rehabilitation activity involving the motion of a limb, a monitoring platform may measure the frequency, rate, and extent of movements of the limb as well as the time of these movements. A similar form of monitoring may be employed for the assessment of exercise being conducted according to an intended form.

Conversely, applications wherein the desired medication is the avoidance of a behavior or activity, the monitoring platform may employ sensors enabling detection of the undesired behavior, e.g. smoking By the absence of measured data that would be in concordance with the undesired activity, the comparator may then assess that the undesired activity has not occurred.

A second aspect of the comparator activities may be the assessing of physiological events resultant in the taking of medication to aid in ascertaining whether inadequate, sufficient or excess amounts of medication have been taken. In broad terms, a medication may have an immediate (or rapid) effect resultant in a desired change in one or more physiological parameters, e.g. improved airway function or cessation of heart arrhythmias. Alternatively, the desired change may take an extended period to occur, e.g. days or weeks such as in the case of many antibiotics or anti-inflammatory drugs. Such temporal issues may or may not be directly associated with the dosage and frequency of the medication.

Figure 4:
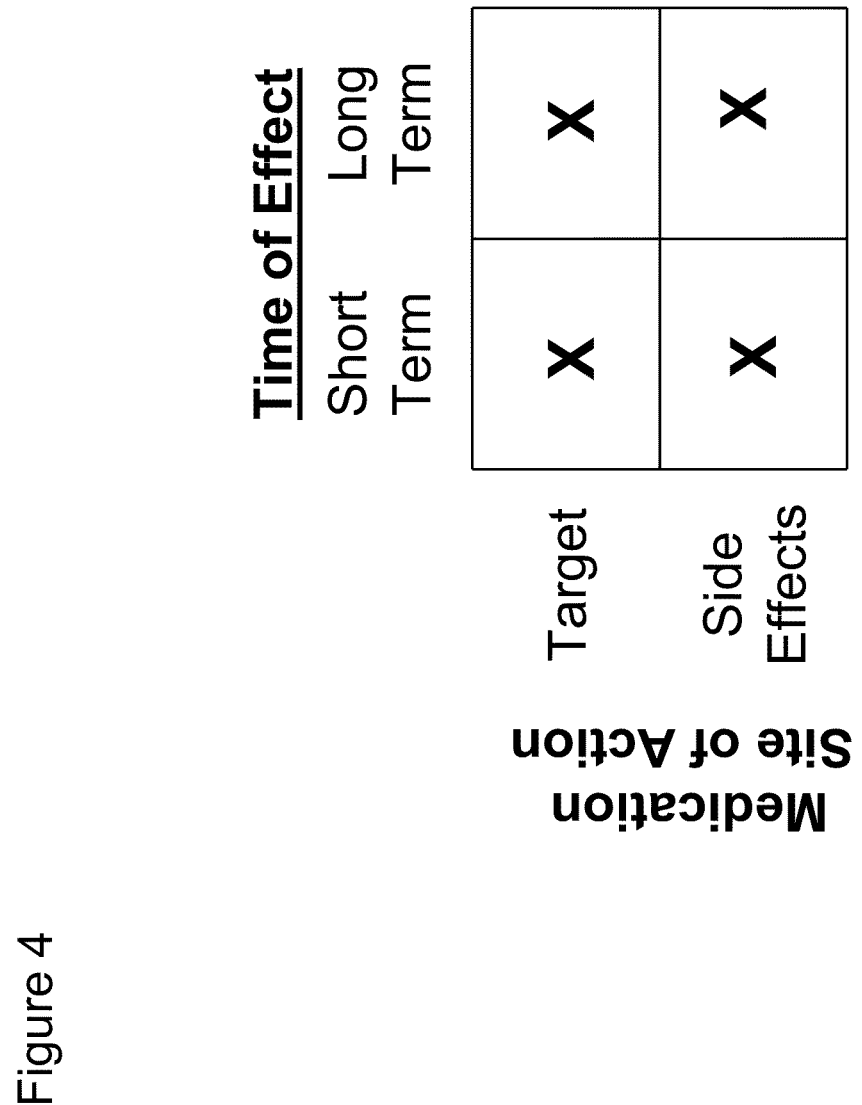
FIG. 4—Illustration of the relationship between medication target and side effects as compared to temporal events.

In similar fashion, side effects of the medication, whether benign or adverse, may occur immediately, or occur after an extended period of time has elapsed. Accordingly, multiple possible scenarios between targeted actions of medications and possible side effects are conceivable. An illustration of this complex relationship between targeted effects and side effects is presented in FIG. 4. In addition, targeted actions and side effects may also depend on the medication dosage and frequency of administration.

To overcome this complexity, in preferred embodiments of the present invention, one or more sets of physiological measurements and/or values derived from these measurements are compiled into data sets termed signatures. By comparison of signatures representative of physiological status in various states, e.g. prior to medication, during the taking of medication and following medication, facilitates comparator assessment as to whether the medication has been taken and whether a desired or non-desired physiological outcome has occurred.

Accordingly, multiple forms of signature may be utilized by the comparator. Forms of these signatures include:

Baseline Signature—Prior to the taking of one or more medications, a baseline series of measurements may be acquired. Factors involved in such measurements may include selected vital signs, e.g. heart rate, respiration rate, blood pressure. In addition, parameters that may be measured and used by the comparator to determine the taking of the medication, its effect and possible side effects may also be measured during this period.

Medication Administration Signature—During a controlled, i.e. defined period during which one or more medications is observed to be taken, one or more physiological measurements may be acquired. These measurements, e.g. of swallowing, heart rate change, etc., may then be utilized by the comparator to facilitate subsequent identification of the taking of medication. In addition, one or more non-physiological measurements, e.g. container opening signals, may be taken and included within the medication administration signature to provide a more complete profile by which to identify subsequent taking of medication.

Medication Effect Signature—Medication is generally targeted to a specific biological endpoint. Accordingly, following the taking of a medication, one or more physiological responses associated with the targeted endpoint may be measured and recorded for subsequent comparative use. Alternatively, targeted endpoints and the associated physiological measurements may be forthcoming from measurements derived from other patients or use scenarios such that the Medication Effect Signature may be available for use by the comparator as a predefined set of parameters and values.

Side Effect Signature—Side effects to the taking of medications may be benign, i.e. without serious health consequences, or may lead to inadvertent adverse health events. As many adverse events may stem from one or more physiological parameters exceeding desired or normative values, use of predefined tabular data may be employed for the construction of side effect signatures tailored to the particular disease state, medication and/or patient population. These signatures in turn may be employed by the comparator to identify and quantify the occurrence and/or progression of one or more side effects.

In a preferred form of the present invention, the comparator may perform a rolling analysis to which data sets representative of time periods are continually evaluated to identify the presence of one or more signatures indicative of one or more of the above possible signature states. This analysis may be performed in a variety of fashions and the present invention is not constrained by any one form or type of mathematical process. For example, a data set may be compared for the degree of similarity to each parameter comprising a signature, e.g. a comparison of temperatures over a period of time.

Alternatively, a comparison may be made between a composite representation, e.g. a multivariate representational line representative of the signature, and the measured data. The degree of closeness or concordance may then be employed to estimate the likelihood that a portion of the data set is representative of a signature event. Such concordance may be determined using one or more mathematical approaches well known to those skilled in the art of statistics. As an extension of this form of comparative evaluation, transforms of data sets, e.g. compressing time scales, etc., may be employed to facilitate matching of one or more data sets to signatures.

Figure 5:
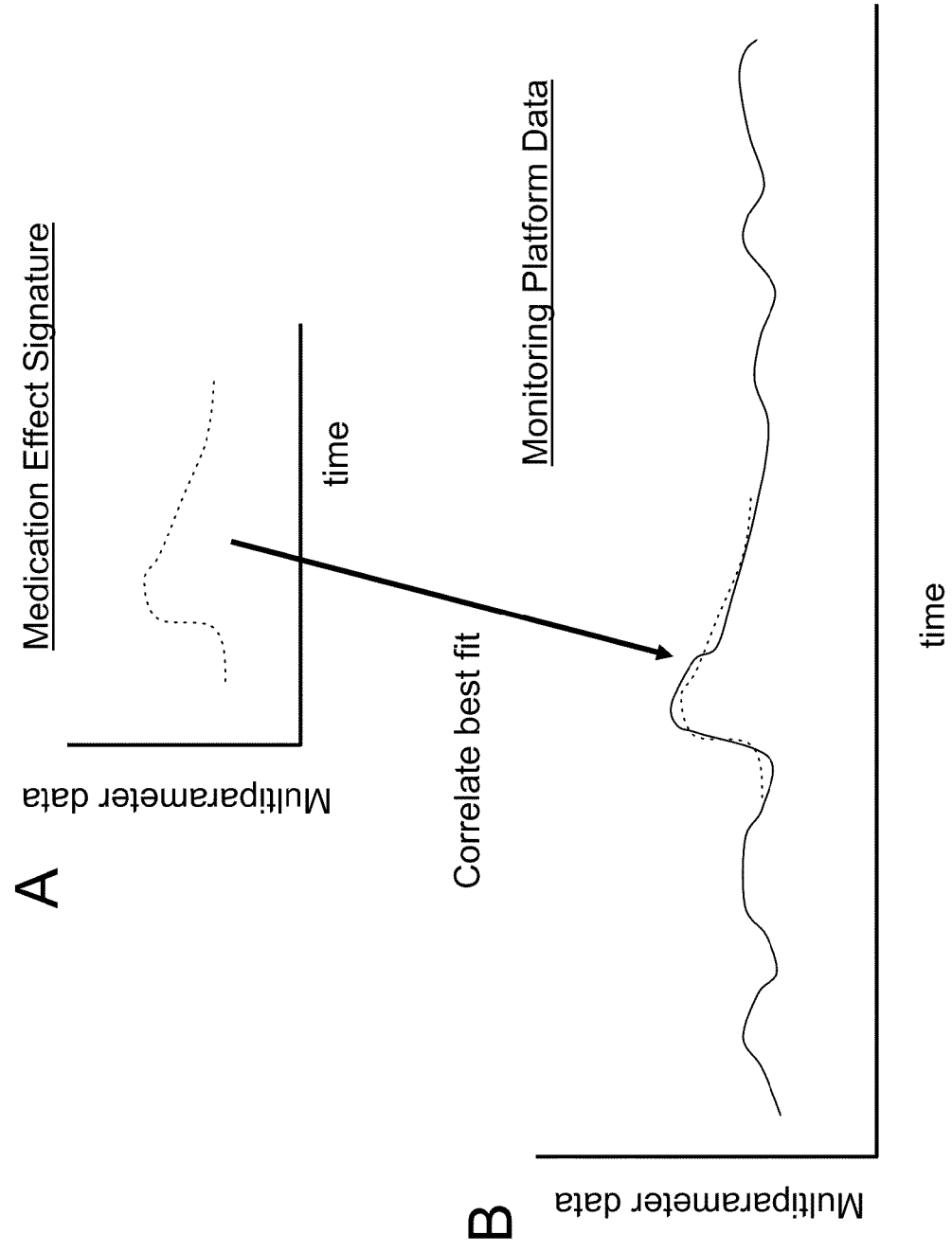
FIG. 5—Illustration of one embodiment of the present invention enabling identification of physiological status associated with a signature.

An illustration of the determination of concordance is presented in FIG. 5. Panel A presents a composite representation of a signature, e.g. a medication effect signature. Panel B presents monitoring platform data obtained over an extended period of time to which the signature is matched. The region exhibiting the highest degree of concordance, e.g. the lowest amount of residual error between signature and observed values, may then be determined to be resultant from the medication. Acceptance of whether the degree of concordance arises to a sufficient level of probability may be performed mathematically using statistical approaches or through qualitative inspection of the data set.

As a further extension, weighting of one or more parameters utilized to describe a signature and/or measured data may be employed to provide greater insight into the likelihood that a signature event has occurred or not.

Alternatively, more simple approaches may be used to determine the extent and likelihood of change from one or more baseline values. Such approaches may use statistical approaches to identify a signature event or change in health status indicative of the taking or not taking medication and/or the result of such taking of medication.

In other forms of the invention, other forms of analyses of physiological and/or other data are employed to identify those measurements associated with the taking of medication and/or physiological consequences from the taking of medication. Such forms of analysis may include the comparative assessment of change in one or more physiological parameters beyond a preset limit and thereby signaling an event such as an undesired side effect. Such events may be scored or scaled to represent the extent of deviation from a baseline value and thereby enable further analysis of patterns or trends within the data set. Such further analysis may include the ranking of the data from parameters, e.g. with certain parameters having more decision weight than others, to facilitate the determination of the likelihood of a medication event or outcome occurring.

In yet other forms of analysis, data from one or more parameters taken at a point in time are represented as a single or multidimensional point. Compilations of such points over time enables cluster analysis wherein drift of data away from clusters representative of baseline conditions may be associated with the taking of medication, relief of symptoms targeted by the medication or the occurrence of one or more side effects.

In a somewhat related form of analysis, trajectory analysis of one or more measured parameters may be employed to facilitate identification of deviations from projected values. Such deviations in turn may be subsequently identified as being associated with one or more events, e.g. the taking of medication, the occurrence of a side effect, etc.

To facilitate the identification of events, one or more approaches may be taken to progressively shift one or more baseline parameters to better accommodate change occurring in the patient's physiological status. Such changes may include change in parameters associated with improvement or degradation of health status. In yet other forms of the invention, such changes may include the removal/replacement of one or more monitoring platforms.

In many forms of analysis, comparison between short term events and long term events and their trends may be made to facilitate the identification of taking of medication and possible physiological changes associated with the taking of medication, e.g. the relief of symptoms and/or the occurrence of side effects. Periods of times describing the length of short term and long term time periods may be predefined to reflect the nature of the disease state, the type of medication employed and the response to the applied medication and anticipated side effects. Alternatively, such discriminations may be made by retrospectively comparing collected data over time to identify these periods as associated with the taking (or not) of medication.

In short, a variety of methods and approaches are available to enable identification of the taking of medication, and the physiological consequences of the taking of medication and the scope of the present invention is not constrained to any one approach or method.

Data and the results of data analysis by the comparator may be displayed in part or in whole on the data collection unit. Alternatively, the data and analysis may be displayed on the remote data management system to enable additional review and further analysis. Such displays may also include alerts, reminders of medication or notifications such that patient status may be noted and responded to in a timely fashion. These alerts, notifications or other responses to data may also be present on the data collection unit.

In yet other embodiments, the remote data management system serves to collect and enable the review of data sets and analyses from a plurality of individuals being monitored. Such collective review and analysis may facilitate the identification of types of physiological states, e.g. adverse events, associated with select patient populations and/or types/dosages of medications.

Figure 6:
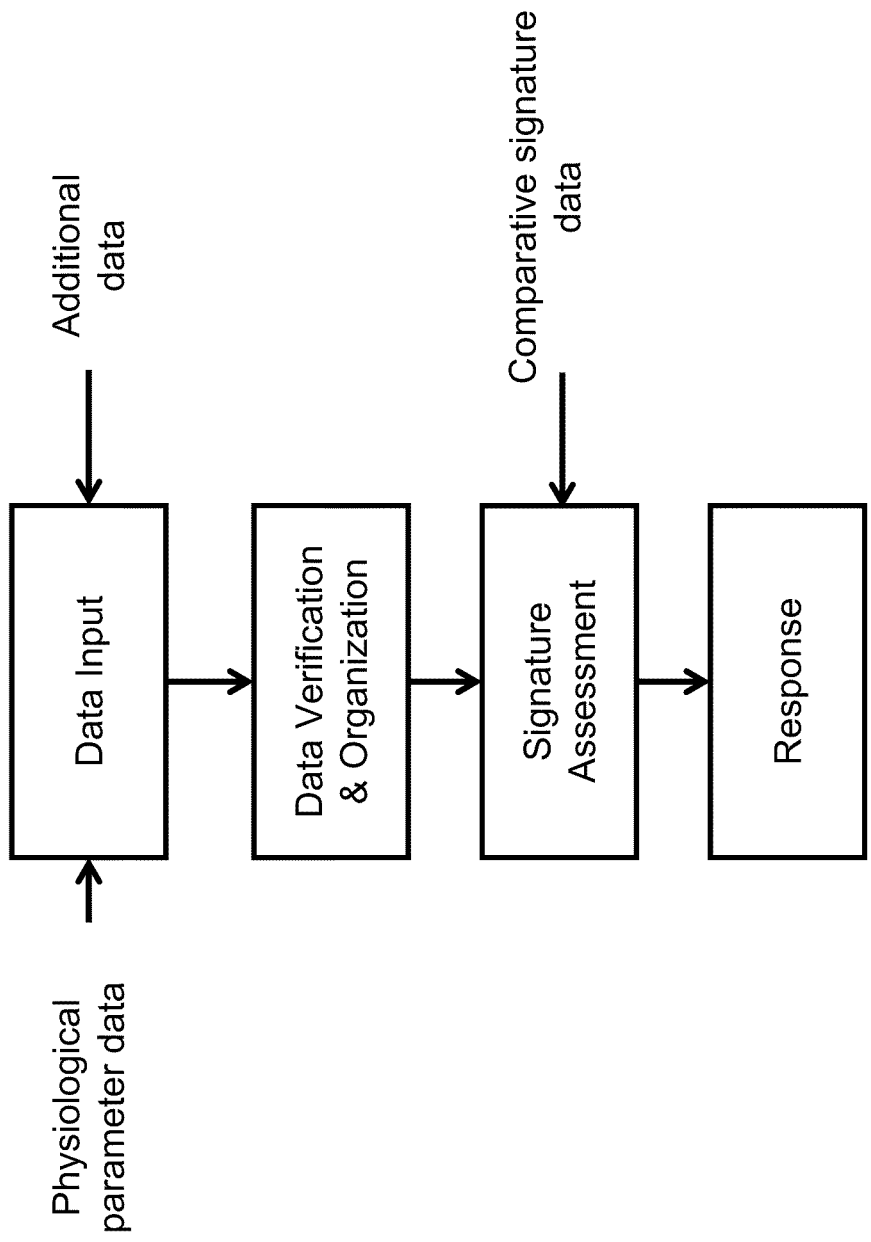
FIG. 6—Illustration of one embodiment of a route by which the comparator receives and processes data.

An outline of a preferred route by which the comparator receives and processes said data is presented in FIG. 6. As shown, the first stage is the data input, e.g. the receiving of information by the comparator generated by one or more sensors and/or inputted to the comparator by an individual. Sensor data may include one or more data received from an on-body monitoring platform. Inputted data may include information useful to the comparator such as identifier associated with the individual and/or additional data regarding the individual's status or condition, e.g. age, gender, co-morbidities. Received data may be held in one or more memory storage or buffers for subsequent stages.

The next stage of the preferred route is the data verification and organization stage. The first portion of this stage is the verification of received data as being appropriate for the data set assembled. For example, data may be erroneously received by the system from sensors not measuring the individual in question. Alternatively, the system may be monitoring a number of individuals and require sorting of data sets according to each individual to enable subsequent analysis. A second component of such verification is to ensure the integrity or completeness of the received data such that incomplete or garbled data is not incorporated into a data base thereby confound subsequent analysis. In receiving sensor data, such data is preferably structured to permit subsequent verification and organization within the comparator.

One such structure facilitating such verification and organization is that of organized fields or segments within the transmitted data block. For example, a first segment may include an identifier specific to the monitoring sensor such that data having such identifiers may be linked to the appropriate individual's data set within the comparator, i.e. through use of one or more look-up tables of previously entered sensor identifiers cross referenced to the individual. A second segment may include information related to the time of data collection or monitoring of the individual, e.g. a time/date stamp, such that received data may be hierarchically assembled in temporal fashion within the comparator's database. A third segment may include the data itself or a representation of the data, e.g. amount of change from previous measured data. A fourth segment may represent a check sum value or other method by which the comparator may verifying completeness of the data as transmitted and received. In related embodiments, one or more identifiers may be utilized to assist in the encryption of the data contained within the transmitted data. Such identifiers may serve as encryption keys utilizable by the comparator to de-crypt the received data.

Upon determination that the received data is appropriate and complete, the third stage of the process is the generation of one or more signatures for assessing whether a medication has been taken or not. As described previously, such signatures may employ data from one or more sensors. Signatures may be composed by assembling a set of sensor data over a period of time previously defined as representative or useful, e.g. heart rate over a 24 hour period encompassing activity and sleep. Once assembled, such data may then be fitted to a curve or mathematical function, e.g. a higher order function having multiple troughs and peaks, to permit comparative analysis to one or more other data sets representative of a similar period of time to establish the degree of difference between the two data sets. Alternative, comparisons may be made on direct comparison between data taken at similar time points or intervals, e.g. heart rate or hydration status at a specific time of day.

Yet another form of signature may employ data from two or more sensors wherein the time component within the period utilized for the signature is normalized in some fashion to enable combination of the two data sets into a single form. For example, hydration change, having a slow basis of change throughout the day, may be normalized relative to percent change from a lowest point within that day, thereby providing a single value representative of the overall range of change. Heart rate, a more rapidly changing parameter, may likewise be normalized to maximal change observed within the day to provide a similar metric representative of the range of change. Once created such normalized data may then be averaged or otherwise mathematically manipulated to provide a single signature value representative of both parameters over this period of time to which other signature values may be compared. It will readily be appreciated that multiple forms of such mathematically manipulations combining two or more types of sensor data are conceivable and that the scope of the present invention is not limited to those examples presented herein.

Once created, a simple form of comparison between signatures may involve the determination of absolute differences in values between the signatures which then may be utilized to determine the average percentage change over the period of time. More elaborate forms of mathematical analysis comparing two or more signatures are conceivable and the scope of the invention is not limited to this one simple example.

Upon determination of differences between two or more signatures, the response or fourth stage of this process occurs. In simple instances, this response may be the recording of the difference into a second data table providing a temporal record of one or more individual's physiological changes relative to one or more signatures over time. Such records may facilitate subsequent analysis of obtained data regarding compliance and/or drug efficacy. A second form of response may be to provide an alert either to the monitored individual or to another party if one or more preset limits are exceeded. For example, if a heart rate signature passes beyond a preset limit, then an alert, e.g. an email or flashing display, may be sent or displayed to one or more individuals to enable possible intervention.

Alternative forms of processing data according the present invention and the scope of the invention is not limited to that example presented herein.

EXAMPLES OF USE

Selected examples of applications and uses are presented below.

Geriatric Medication—Seniors or other individuals may have difficulty complying in taking one or more medications. Accordingly one form of the present invention may include the use of a monitoring platform affixed to the individual plus a data collection unit configured to be readily employed by the elderly, e.g. large type font, clear instructions.

Upon programming of the data collection unit, e.g. by a clinician or care giver, the system will monitor the basic health parameters, e.g. nutritional status, activity, selected vital signs, etc. plus possible hallmarks specific to the prescribed medication, e.g. heart rhythm and pacing. Review of analyzed data will then aid in ensuring the proper taking of medication.

Drug Study Compliance—Evaluation of the efficacy of new medications is facilitated by the knowledge that the study volunteers are adhering to the recommended medication regimen, e.g. taking the test medicines at the appropriate times. The present invention would facilitate this evaluation by improving the knowledge that test medications are being taken (or not) by the study volunteers. In addition, the monitoring of multiple physiological parameters may enable early detection of one or more unforeseen side effects associated with the medication. Such early detection may enable either adjustment of the study and/or cessation of the study, thereby improving study participant safety.

Corporate Wellness Program Participation—Participation by individuals in corporate wellness programs may be improved by the use of monitoring systems such as the present invention. In particular, programs promoting increased exercise and/or smoking cessation may be improved by increased compliance by participants. In particular, the knowledge of participants that the system is monitoring their activity and general health status may provide extra incentive to adhere to recommended medication (therapy guidance). In addition, the ability of the monitoring platform, if continually affixed to the participant, enables the creation of set of physiological data specific to the individual. Such individual data sets may serve as an identifier such that the participant is less likely to try to have another individual wear the monitoring platform and thereby deceive or trick the system, i.e. the identifier would enable comparator detection and subsequent alert.

Chronic Illness Monitoring—For individuals suffering from a chronic illness, e.g. congestive heart failure, Parkinson's disease, etc., knowledge by clinicians of patient compliance to prescribed medications and the effectiveness of these medications is useful. Accordingly, the present invention may be employed to monitor these individuals over extended periods of time to better enable assessment of medication effectiveness and/or enable intervention to improve patient health status.

A variety of applications, based upon the present invention, are readily conceivable and the scope of the invention is not limited to the examples presented above.

What is claimed is:

1. A method for quantifying the effect of a medication on a patient, the method comprising:
   providing a monitoring platform capable of measuring one or more physiological parameters;
   obtaining a first set of measurements of the physiological parameters from the patient by using the monitoring platform to measure the physiological parameters during a first period of time;
   compiling a first signature from a first set of data including the first set of measurements; and
   comparing the first signature with a second signature to determine acceptance of whether a degree of concordance rises to a sufficient level of probability that a change has occurred in the physiological parameters;
   wherein the second signature is compiled from a second set of data including a second set of measurements of the physiological parameters obtained from the patient during a second period of time.

2. The method of claim 1, wherein a non-physiological event has occurred between the first period of time and the second period of time.

3. The method of claim 2, wherein the non-physiological event is a signal associated with removal of the medication from a container.

4. The method of claim 2, wherein the non-physiological event is a signal associated with a delivery of the medication.

5. The method of claim 1, wherein the second signature is a signature associated with a degradation in health status.

6. The method of claim 1, wherein compiling a first signature includes weighting each of the physiological parameters.

7. The method of claim 1, wherein the first set of data further includes one or more of age, gender, and co-morbidities.

8. The method of claim 1, wherein the obtaining a first set of measurements includes obtaining a first set of measurements for one or more periods of time having different lengths.

9. The method of claim 1, wherein the medication is a therapy or an activity.

10. The method of claim 1, wherein the medication is the avoidance of a behavior or an activity.

11. A method for quantifying the effect of a medication on a patient, the method comprising:
    providing a monitoring platform capable of measuring one or more physiological parameters;
    obtaining a first set of measurements of the physiological parameters from the patient by using the monitoring platform to measure the physiological parameters;
    compiling a first signature from a first set of data including the first set of measurements; and
    comparing the first signature with a second signature to determine acceptance of whether a degree of concordance rises to a sufficient level of probability that a change has occurred in the physiological parameters;
    wherein the second signature is a predefined signature compiled from a second set of data including a second set of measurements of the physiological parameters obtained from one or more other patients.

12. The method of claim 11, wherein the predefined signature is a medication effect signature compiled from a second set of data including targeted endpoints for the physiological parameters.

13. The method of claim 11, wherein the predefined signature is a side effect signature compiled from predefined tabular data for the physiological parameters.

14. The method of claim 11, wherein compiling a first signature includes weighting each of the physiological parameters.

15. The method of claim 11, wherein the first set of data further includes one or more of age, gender, and co-morbidities.

16. The method of claim 11, wherein the obtaining a first set of measurements includes obtaining a first set of measurements for one or more periods of time having different lengths.

17. The method of claim 11, wherein the medication is a therapy or an activity.

18. The method of claim 11, wherein the medication is the avoidance of a behavior or an activity.

19. A method for quantifying the effect of a medication on a patient, the method comprising:
    providing a monitoring platform capable of measuring one or more physiological parameters;
    obtaining a first set of measurements of the physiological parameters from the patient by using the monitoring platform to measure the physiological parameters during a first period of time;
    compiling a first signature from a first set of data including the first set of measurements; and
    comparing the first signature with a second signature to determine acceptance of whether a degree of concordance rises to a sufficient level of probability that a change has occurred in the physiological parameters;
    wherein the second signature is a composite representation compiled from a second set of data including a second set of measurements of the physiological parameters obtained from the patient during a second period of time.

20. The method of claim 19, wherein the composite representation is a multivariate representational line representative of the signature compiled from a second set of data including a second set of measurements of the physiological parameters.

* * * * *